(12) United States Patent
Albrecht et al.

(10) Patent No.: US 12,721,750 B2
(45) Date of Patent: Sep. 1, 2026

(54) CONTROLLED INJECTION BETWEEN TWO TISSUE LAYERS OF THE HUMAN EYE

(71) Applicant: Carl Zeiss Meditec AG, Jena (DE)

(72) Inventors: Christian Albrecht, Aalen (DE); Sophie Wurst, Michelbach a.d. Bilz (DE)

(73) Assignee: CARL ZEISS MEDITEC AG, Jena (DE)

( * ) Notice: Subject to any disclaimer, the term of this patent is extended or adjusted under 35 U.S.C. 154(b) by 624 days.

(21) Appl. No.: 18/008,359

(22) PCT Filed: May 27, 2021

(86) PCT No.: PCT/EP2021/064275
§ 371 (c)(1),
(2) Date: Dec. 5, 2022

(87) PCT Pub. No.: WO2021/249785
PCT Pub. Date: Dec. 16, 2021

(65) Prior Publication Data

US 2023/0277374 A1 Sep. 7, 2023

(30) Foreign Application Priority Data

Jun. 9, 2020 (DE) .................... 10 2020 115 346.5

(51) Int. Cl.
*A61F 9/00* (2006.01)
*A61F 9/007* (2006.01)
(Continued)

(52) U.S. Cl.
CPC ........ *A61F 9/0017* (2013.01); *A61F 9/00727* (2013.01); *A61B 2017/00017* (2013.01);
(Continued)

(58) Field of Classification Search
CPC .......... A61F 9/00; A61F 9/007; A61F 9/0008; A61M 5/142; A61M 5/168; A61M 2005/14208; A61M 2210/0612
See application file for complete search history.

(56) References Cited

U.S. PATENT DOCUMENTS 5,066,276 A 11/1991 Wang
5,091,037 A 2/1992 Soikkeli
(Continued)

FOREIGN PATENT DOCUMENTS

EP 3471670 10/2020
GB 2543645 4/2017
(Continued)

OTHER PUBLICATIONS

Nasseri et al., "A targeted drug delivery platform for assisting retinal surgeons for treating Age-related Macular Degeneration (AMD)," 39th Annual International Conference of the IEEE Engineering in Medicine and Biology Society (EMBC), 2017, pp. 4333-4338.
(Continued)

*Primary Examiner* — Laura A Bouchelle
(74) *Attorney, Agent, or Firm* — NIXON PEABODY LLP; Jeffrey L. Costellia

(57) ABSTRACT

A control device for controlling and/or regulating an injection flow rate, when injecting a fluid at an injection site between two tissue layers of the human eye with an injection flow rate that increases with time, is described, which comprises a controlling or regulating unit configured to control the injection flow rate in such a way that the injection flow rate increases during the injection for at least 30% of the injection time or during the injection of at least 30% of the injection volume.

15 Claims, 5 Drawing Sheets

Figure 1:
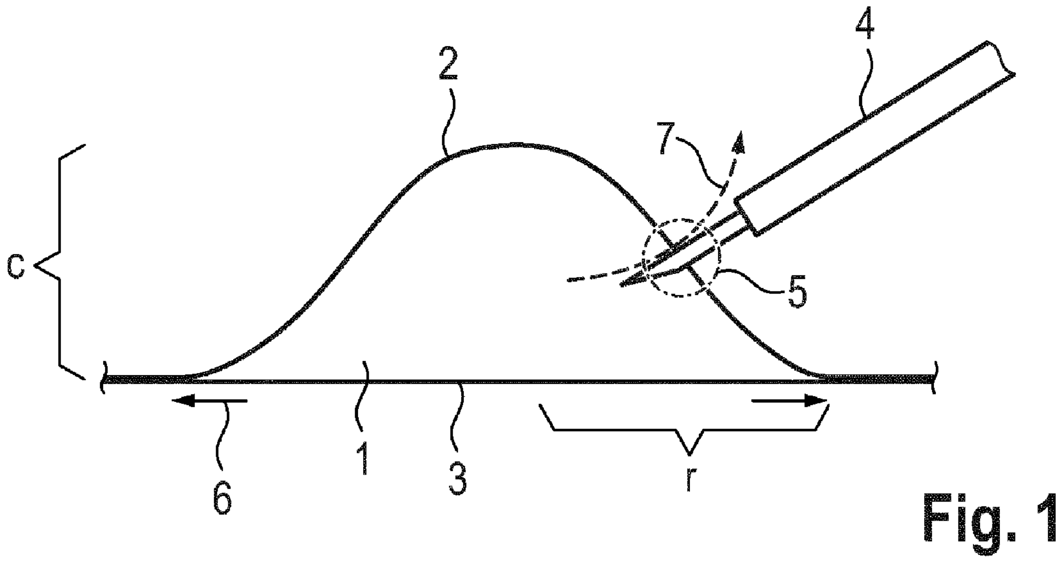

(51) Int. Cl.

| | |
|---|---|
| *A61B 17/00* | (2006.01) |
| *A61B 90/00* | (2016.01) |
| *A61M 5/142* | (2006.01) |
| *A61M 5/168* | (2006.01) |

(52) U.S. Cl.

CPC ........ *A61B 2090/064* (2016.02); *A61M 5/142* (2013.01); *A61M 2005/14208* (2013.01); *A61M 5/168* (2013.01)

(56) References Cited

U.S. PATENT DOCUMENTS

| | | | | |
|---|---|---|---|---|
| 11,759,355 | B1 * | 9/2023 | Keane ................ | A61F 9/00727 604/506 |
| 2003/0055685 | A1 | 3/2003 | Cobb et al. | |
| 2015/0164687 | A1 | 6/2015 | Kashani et al. | |
| 2018/0256393 | A1 | 9/2018 | Yamamoto et al. | |

FOREIGN PATENT DOCUMENTS

| | | |
|---|---|---|
| JP | 2003-290343 | 10/2003 |
| WO | WO-2014/168216 | 10/2014 |
| WO | WO-2016/061569 | 4/2016 |

OTHER PUBLICATIONS

Williams et al., "A New Method of Subretinal Injection of Tissue Plasminogen Activator and Air in Patients With Submacular Hemorrhage," Surgical Technique, Retina, The Journal of Retinal and Vitreous Diseases, 2017, vol. 37, No. 8, pp. 1607-1611.
German Office Action for Application No. 10 2020 115 346.5, mailed Mar. 22, 2021 (12 pages).
Written Opinion for Application No. PCT/EP2021/064275, mailed Sep. 7, 2021 (16 pages).
International Search Report for Application No. PCT/EP2021/064275, mailed Sep. 7, 2021 (6 pages).
Office Action in Chinese Patent Application No. 202180041246.1 with English Translation, dated Oct. 10, 2025, (35 pages).

* cited by examiner

CONTROLLED INJECTION BETWEEN TWO TISSUE LAYERS OF THE HUMAN EYE

CROSS-REFERENCE TO RELATED APPLICATIONS

The present application is the U.S. national stage entry of International Application No. PCT/EP2021/064275, filed May 27, 2021, which claims the benefit of and priority to German Patent Application No. 10 2020 115 346.5, filed Jun. 9, 2020, the contents of which are incorporated by reference herein in their entirety.

The present invention relates to a control apparatus for open-loop and/or closed-loop control of an injection flow rate when injecting a fluid, that is to say a liquid or a gas, at an injection site between two tissue layers of the human eye, for example between the neural layer of the retina and the retinal pigment epithelium. The invention further relates to an apparatus for injecting a fluid at an injection site between two tissue layers of the human eye, for example between the neural layer of the retina and the retinal pigment epithelium, to a computer program, to a non-volatile computer-readable storage medium, to an arrangement for performing ophthalmic operations and to a method for open-loop and/or closed-loop control of the injection flow rate when injecting a fluid at an injection site between two tissue layers of the human eye, for example between the neural layer of the retina and the retinal pigment epithelium. The two tissue layers of the human eye are also referred to below as the first layer and second layer.

In the case of a subretinal injection, liquid is introduced between the neural layer of the retina (NR) and the retinal pigment epithelium (RPE) by means of a cannula. This exploits the fact that the interaction between the neural layer of the retina and the retinal pigment epithelium is based on relatively weak molecular bonds, which leads to a detachment of the neural layer of the retina even with small pressure differences between the subretinal space and the intraocular pressure. This leads to the formation of a liquid-filled bubble, a so-called bleb, which can extend over the entire fundus.

Typical applications of a subretinal injection are the dissolution of subretinal hemorrhages by injecting plasminogen activator and air, and gene therapy interventions in which viral gene vectors are introduced, and stem cell therapy. Examples of this are described, in particular, in the publication by Wilhelms, George A., "*A New Method of Subretinal Injection of Tissue Plasminogen Activator and Air in Patients With Submacular Hemorrhage*", Retina. 2017 August 37 (8), pages 1607 to 1611.

Typical volumes for subretinal injections are between 100 microliters and 400 microliters (100 μl-400 μl). However, the injection volume may also be limited to volumes of less than 100 microliters in the case of certain clinical pictures, such as age-related macular degeneration (AMD). By way of example, this is necessary when "islands" of intact macula are surrounded by degenerated retinal pigment epithelium.

The most commonly used access to the subretinal space is transscleral through the pars plana (region on the sclera that extends around the ciliary body), piercing the vitreous humor and neuroretina with a straight cannula. Ideally, the neural layer of the retina and the retinal pigment epithelium separate in a smooth process during injection. It is important in the process that the valuable injection liquid is transferred as completely as possible into the so-called bleb, and also remains there after the needle of the cannula has been removed. However, the measurement of blebs using optical coherence tomography (OCT) has shown that significant volume losses may occur. This means that the volumes of the blebs are smaller than the volume of liquid applied, for example a buffer with the viral gene vector. This is to be avoided, especially given the significant costs of the liquids to be injected.

Document U.S. Pat. No. 5,091,037 A describes a pneumatically operated injector for ophthalmic therapies in conjunction with retinopexy, which is used for the partial repair of partially detached and/or torn retinas. Document GB 2 543 645 A describes an injection device for ophthalmic applications, wherein increasing actuation of the provided valve actuation mechanism increases the flow rate of the injection. Sealing the puncture site by means of a sealing element is also described.

Against the background described, it is an object of the present invention to make available an advantageous apparatus for providing an injection flow rate when injecting a liquid at an injection site between the neural layer of the retina and the retinal pigment epithelium, by means of which the described volume losses of the liquid to be injected are reduced, in particular without a sealing element being required at the distal end. At the same time, the duration of the injection, that is to say in particular the state in which the cannula or syringe used penetrates the neuroretina, should be as short as possible, that is to say preferably reduced. Further objects consist of making available a computer program, an arrangement for carrying out ophthalmic operations, and a method for controlling the injection flow rate.

The stated objects are achieved by a control apparatus for open-loop and/or closed-loop control of an injection flow rate when injecting a fluid, for example a liquid or a gas, at an injection site between two tissue layers of the human eye as claimed in patent claim 1, a computer program as claimed in patent claim 11, an arrangement for performing ophthalmic operations as claimed in patent claim 12, and a method for open-loop and/or closed-loop control of the injection flow rate when injecting a liquid at an injection site between two tissue layers of the human eye as claimed in patent claim 13. The dependent claims contain further advantageous designs of the invention.

In the context of trials on pig eyes in connection with the present invention, it was found that a high volume loss correlates with high flow rates. This insight is also part of the invention. What was found here in the examined examples is that flow rates of the order of less than 10 microliters per second (<10 μl/s) lead to volume losses of more than 50%. However, with the lowest injection flow rate of approximately 0.1 microliter per second (0.1 μl/s), the volume loss is less than 10%. OCT images of injections with high flow rates and a contrast medium in the buffer indicate that the volume loss occurs primarily in the initial phase, that is to say before a clearly recognizable bleb has formed once the needle has been inserted. In this respect, a leak can be assumed, that is to say injected solution escapes from the side of the cannula through the retinotomy instead of being received in the subretinal space.

Furthermore, trials have shown that the volume loss is lower at low flow rates than at high flow rates. However, a low inflow, that is to say a low injection flow rate, also results in very long injection times. By way of example, it takes about 17 minutes to inject 100 microliters (100 μl) of a liquid into the subretinal space in the case of an injection flow rate of 0.1 microliter per second (0.1 μl/s). Such a long time is undesirable for manual injections, since the cannula cannot be kept still by the surgeon over long periods of time. Even if a robotic manipulator were used, the lengthening of the operation resulting from the low injection flow rate would be disadvantageous for the patient.

What was determined within the scope of the present invention is that the fact that volume is lost in the case of high flow rates can probably be traced back to the fact that the rate with which the tissue layers can be separated from one another is inherently limited. This means that the resistance of the tissues to separation increases sharply above a critical separation rate. As a result, the inflow of liquid per unit of time can no longer be compensated for by a corresponding increase in radius and thus an increase in volume of the bleb. As a result, an overpressure develops in the bleb, which is compensated for by leakage currents in the region of the puncture site. In fact, in the case of injections with high flow rates and high volume loss, a sudden increase in the pressure in the bleb could be registered.

The control apparatus according to the invention for open-loop and/or closed-loop control of an injection flow rate when injecting a fluid, for example a liquid or a gas, at an injection site between two tissue layers of the human eye, for example between the neural layer of the retina and the retinal pigment epithelium, with an injection flow rate increasing over time comprises an open-loop or closed-loop control unit. The open-loop or closed-loop control unit is designed for open-loop or closed-loop control of the injection flow rate, in such a way that the injection flow rate increases during the injection for at least 30 percent (30%) of the injection time, in particular at least 50%, preferably at least 65% of the injection time, or increases during the injection of at least 30 percent (30%) of the injection volume, in particular at least 50%, preferably at least 65% of the injection volume. The injection flow rate can increase continuously and in particular strictly monotonically here, but it can also increase in steps, that is to say the injection flow rate increases during the injection for at least 30 percent (30%) of the injection time, in particular at least 50%, preferably at least 65% of the injection time, or during the injection of at least 30 percent (30%) of the injection volume, in particular at least 50%, preferably at least 65%, of the injection volume in several steps, with it being advantageous for a continuously increasing injection flow rate to be approximated by a multiplicity of steps, each with a small increase. The injection is preferably carried out in such a way that a bubble filled with the fluid, that is to say a so-called bleb, forms between the tissue layers, for example the neural layer of the retina and the retinal pigment epithelium. Injection time is understood as the time during which the utilized injection needle penetrates the tissue and fluid is delivered by means of the needle.

Advantageously, an initial injection flow rate does not exceed a value of 5 microliters per second (5 μl/s) here. Preferably, the initial injection flow rate is no more than 1 μl/s, in particular no more than 0.1 μl/s, more particularly no more than 0.05 μl/s. By way of example, the initial injection flow rate may remain constant for a defined injection time, for example 10 seconds (10 s), in particular 5 s, preferably 2 s, or until an input signal is received. In this case, the input signal can be generated in automated fashion, for example using an optical coherence tomography (OCT) device or within the scope of image analysis, for example if a bleb is detected. In addition or as an alternative, the input signal can be generated manually, for example triggered by a user. A typical lower value for the initial injection flow rate would be in the range of 0.001 μl/s to 0.01 μl/s and could be 0.001 μl/s, 0.005 μl/s or 0.01 μl/s, for example.

In an advantageous development of the invention, a maximum injection flow rate reached during the injection does not exceed a value of 100 microliters per second (μl/s). In particular, the maximum injection flow rate reached during the injection can be in the range between 5 μl/s and 100 μl/s, in particular between 15 μl/s and 80 μl/s, for example 25 μl/s, 50 μl/s or 80 μl/s, with the maximum injection flow rate reached during the injection usually being higher as the injected volume increases. Typically, the volumes injected during the injection are in the range between 100 μl and 500 μl, with a volume of 500 μl injected during the injection tending to reach maximum injection flow rates in the range of 70 μl/s to 100 μl/s and with a volume of 100 μl injected during the injection tending to reach maximum injection flow rates in the range of 5 μl/s to 25 μl/s. In the case of a maximum injection flow rate of 5 μl/s reached during the injection, the initial injection flow rate naturally has a value of less than 5 μl/s, for example a value of no more than 1 μl/s, in particular no more than 0.1 μl/s, further particularly no more than 0.05 μl/s.

In a further variant, an initial injection can take place with a defined upper limit value for the initial injection flow rate, followed by an injection with an injection flow rate increasing above the defined upper limit value. The upper limit value is preferably no more than 5 microliters per second, in particular no more than 1 microliter per second, advantageously no more than 0.25 microliter per second or less. The open-loop or closed-loop control unit can be designed for mechanical or electronic open-loop and/or closed-loop control of the injection flow rate.

The control apparatus according to the invention has the advantage that it enables subretinal injections, in which, first of all, the volume loss of the injected fluid can be reduced, preferably minimized, and, at the same time, the injection time can be optimized, that is to say in particular can be minimized with respect to the lowest possible volume flow of the fluid to be injected.

The open-loop or closed-loop control unit can be designed for open-loop or closed-loop control of the increasing injection flow rate, in such a way that an injection takes place with a constant or variable gradient of the injection flow rate of between 2 and 100. The increase in the injection flow rate can be linear or nonlinear, for example quadratic or cubic or polynomial. The initial injection flow rate can be a constant injection flow rate.

The apparatus according to the invention may have two operating modes. A first operating mode is then designed to provide a low injection flow rate below the defined upper limit value, for example a constant injection flow rate. A second operating mode is designed to provide an increasing injection flow rate, preferably provide an injection flow rate that increases, for example continuously increases, starting from the constant injection flow rate. The order of operation of the mentioned operating modes is variable, but preferably the second operating mode is put into operation after the first operating mode. However, a change, in particular a temporary change, from the second to the first operating mode is also possible and advantageous under certain circumstances.

In one variant, the control apparatus is designed to control the increasing injection flow rate according to a predetermined curve, for example a characteristic curve of the injection flow rate as a function of at least one parameter, such as the time, the injection pressure, or the radius of a bleb that forms during the injection.

In a further variant, the control apparatus is designed to determine and provide a current injection flow rate on the basis of the current value of at least one parameter that characterizes the current tissue separation rate and on the basis of a predetermined tissue separation rate. The predetermined tissue separation rate can be a limit value of a tissue separation rate, for example a critical tissue separation rate, at which a defined volume loss of the injected fluid maximally occurs. The critical tissue separation rate is determined by the adhesion forces between the two tissue layers and is determinable experimentally or by model calculations. Preferably, the predetermined tissue separation rate may be a tissue separation rate at which there is a minimal volume loss of the injected fluid. The predetermined tissue separation rate can be determined and/or defined in advance. Preferably, the predetermined tissue separation rate is between 0.01 and 1 mm/s, in particular between 0.01 and 0.3 mm/s. In an advantageous variant, the control apparatus is designed to determine and provide a current injection flow rate at which the predetermined tissue separation rate is not exceeded. By not exceeding a predetermined tissue separation rate, which does not exceed the critical tissue separation rate, it is possible to ensure that a specific pressure in the forming bleb is not exceeded during the injection and leakage currents that are potentially caused as a result can be avoided. This also reduces considerable costs for the injection fluid, which as a rule is very expensive.

In a further advantageous variant, the control apparatus comprises a device for recording and/or displaying the current value of the at least one parameter of the bleb or the injection parameter or the parameter characterizing the current tissue separation rate. In this case, the device for recording the current value of the at least one parameter can be designed to record a property of the bleb forming during the injection and/or an injection parameter as a parameter. The property of the bleb can be, in particular, a parameter characterizing the geometry of the bleb, for example the volume and/or the radius and/or the height. However, this can also be the pressure in the bleb. By way of example, the injection flow rate or the injection pressure can be recorded as an injection parameter, that is to say the device for recording the current value can be designed to record these.

In an exemplary variant, the device for recording the current value of the at least one parameter can be designed to display an image and/or the geometry and/or the volume of the bleb and/or display or electronically provide a value for the radius and/or the height of the bleb or the pressure in the bleb or the injection pressure or the injection flow rate. The device for recording the current value of the at least one parameter can include, for example, an apparatus for generating an image of the injection site.

The apparatus for generating an image of the injection site can be a microscope, for example an ophthalmic microscope, and/or an optical coherence tomography (OCT) device, for example an intraoperative optical coherence tomography device. The apparatus for generating an image of the injection site can furthermore be designed to provide information about the properties of the bleb that arises or is formed during the injection. The information to be provided can be values for the parameters already mentioned, that is to say for example the geometry, the volume or the radius. However, it can also be the current tissue separation rate. These values can be determined, for example, by means of algorithms for digital image analysis.

In addition or as an alternative to the aforementioned variants, the device for recording a current value of the at least one parameter may comprise a pressure sensor for determining the injection pressure, that is to say the pressure of the injected fluid. Advantageously, the pressure sensor is arranged on a cannula used for the injection or as close as possible to such a cannula.

The presence of a device for recording a current value of the at least one parameter, that is to say in particular an apparatus for generating an image of the injection site and/or a pressure sensor, is advantageous in that this allows determination of the current point on a predetermined curve of the increasing injection flow rate as a function of at least one parameter. This makes it possible to ensure in a particularly effective manner that the volume flow caused by the increasing injection flow rate does not exceed the maximum rate at which the volume of the bleb can change.

The control apparatus can be designed for manual or automated open-loop and/or closed-loop control of the injection flow rate. In particular, the control apparatus can be designed for open-loop or closed-loop control of the increasing injection flow rate, in such a way that the predetermined tissue separation rate dr/dt is not exceeded and/or that the tissue separation rate dr/dt is kept constant and/or that the injection pressure is kept constant. The maximum rate at which the volume of the bleb can change results from the critical tissue separation rate. By specifying a tissue separation rate that does not exceed the critical tissue separation rate, it is therefore possible to ensure that the rate at which the volume of the bleb can change can keep up with the fluid volume introduced by the increasing injection flow rate.

In a particularly advantageous variant, the control device is designed for open-loop and/or closed-loop control of the increasing injection flow rate, in such a way that the fluid is injected at an injection flow rate $Q=dV/dt$, where Q denotes the injection flow rate, V denotes the volume of the bleb and t denotes the time, which injection flow rate is increased proportionally to a power n of the radius r of the bleb ($Q\sim r^n$), where the power n is preferably greater than 1 and no more than 2 ($1<n\leq 2$), and the proportionality factor is based on the predetermined tissue separation rate dr/dt. The power is preferably 2. The above-described open-loop or closed-loop control can also be implemented in particular within the scope of the aforementioned second operating mode in connection with a recorded current value of a parameter which characterizes the current radius r of a bleb forming during the injection.

An above-described open-loop or closed-loop control of the increasing injection flow rate is advantageous in that the increasing injection flow rate during the injection is increased as a function of the radius of the bleb, in such a way that the smallest possible volume loss occurs in the introduced fluid and the injection time can be kept as short as possible in the process. In this context, the control apparatus can be designed, for example within the scope of the second operating mode in conjunction with a current value of a parameter which characterizes the current radius of the bleb and/or the current volume of the bleb, for open-loop and/or closed-loop control of the increasing injection flow rate on the basis of the radius r and/or the volume V of the bleb, in such a way that an injection flow rate resulting at the predetermined tissue separation rate from a curve for the increasing injection flow rate as a function of the radius r of the bleb and/or the volume of the bleb is not exceeded for the respective radius and/or the respective volume.

In a further variant, the control apparatus is designed for open-loop and/or closed-loop control of the increasing injection flow rate as a function of time, in such a way that an injection flow rate resulting from a defined curve is set and/or not exceeded for each point in time from the start of the injection. The control device can therefore preferably be designed for open-loop and/or closed-loop control of the increasing injection flow rate which is as close as possible to one of the aforementioned curves, in particular to increase said increasing injection flow rate during the injection on the basis of the time and/or the radius. This allows the injection time and, at the same time, the volume loss to be minimized.

The control apparatus can be part of an apparatus for injecting a fluid at an injection site between two tissue layers of the human eye.

The apparatus according to the invention for injecting a fluid at an injection site between two tissue layers of the human eye, for example between the neural layer of the retina and the retinal pigment epithelium, in such a way that the first layer separates from the second layer at a tissue separation rate and a bleb, that is to say a bubble filled with the fluid, forms, comprises a microsyringe and an actuation device for actuating the microsyringe. The microsyringe used can have a diameter of between 0.05 and 0.75 mm, in particular 0.07 to 0.09 mm, for example 0.0711 mm (41G). The apparatus according to the invention for injecting a fluid is distinguished in that there is an above-described control apparatus according to the invention for open-loop and/or closed-loop control of the injection flow rate present, which is connected to the actuation device. The actuation device can also include the control device according to the invention.

The apparatus according to the invention for injecting a fluid at an injection site between two tissue layers of the human eye has the advantages already mentioned above. In particular, it enables an injection with a low volume loss and within a time period that is optimized in relation to the desired, maximally low volume loss. The injection can therefore be carried out as quickly and efficiently as possible using the apparatus according to the invention.

The actuation device may comprise a foot pedal. The actuation device may be designed to provide pneumatic pressures between 10 and 20 mmHg, that is to say between 0.013 and 2.67 bar. The increasing injection flow rate can be flexibly controlled by a suitable variability of the injection pressure.

The computer program according to the invention for open-loop and/or closed-loop control of an injection flow rate when injecting a fluid at an injection site between two tissue layers of the human eye with an increasing injection flow rate comprises instructions which, when executed on a computer, cause the latter to control the injection flow rate in such a way that the injection flow rate increases during an injection for at least 30%, in particular at least 50%, preferably at least 65%, of the injection time or during the injection of at least 30%, in particular at least 50%, preferably at least 65% of the injection volume. In particular, the instructions, when executed on a computer, can cause the latter to control the injection flow rate in such a way that an initial injection occurs with a defined upper limit value for the initial injection flow rate, followed by an injection with an injection flow rate increasing above the defined upper limit value.

The non-volatile computer-readable storage medium according to the invention comprises instructions for open-loop and/or closed-loop control of an injection flow rate when injecting a fluid at an injection site between two tissue layers of the human eye with an increasing injection flow rate stored thereon which, when executed on a computer, cause the latter to control the injection flow rate in such a way that the injection flow rate increases during an injection for at least 30%, in particular at least 50%, preferably at least 65%, of the injection time or during the injection of at least 30%, in particular at least 50%, preferably at least 65% of the injection volume. In particular, the instructions, when executed on a computer, can cause the latter to control the injection flow rate in such a way that an initial injection occurs with a defined upper limit value for the initial injection flow rate, followed by an injection with an injection flow rate increasing above the defined upper limit value.

The computer program according to the invention and the non-volatile computer-readable storage medium according to the invention have the features and advantages already mentioned above.

The arrangement according to the invention for performing an ophthalmic operation comprises a device for generating an image of the injection site and an apparatus according to the invention, already described above, for injecting a fluid at an injection site between two tissue layers of the human eye. In this case, the device for generating an image of the injection site is connected to, or comprised by, the control apparatus for signal transmission purposes. As already mentioned above, the device for generating an image of the injection site can be a microscope, for example an ophthalmic microscope, and/or an optical coherence tomography device, for example an intraoperative OCT device.

The arrangement according to the invention for performing ophthalmic operations has the advantages already mentioned. It enables particularly efficient subretinal injections for a patient in particular, within the scope of which the fluid to be injected can be performed with little volume loss and the shortest possible injection duration. By means of the arrangement according to the invention for performing ophthalmic operations, corresponding operations become more economical with regard to the consumption of the fluid to be injected since injection losses are reduced. The duration of the operation is optimized at the same time, and so an increase in efficiency is also made possible in this respect.

Like the control apparatus according to the invention, the apparatus according to the invention for injecting a fluid at an injection site or the arrangement according to the invention for performing an ophthalmic operation can comprise a display. The display may be configured to show a target value and an actual value, as used by the user, for the injection flow rate. A corresponding display is advantageous in that a user can also manually control the increasing injection flow rate. In particular, the target value can be determined by means of a predetermined curve for the injection flow rate on the basis of the geometry of the bleb, for example the current radius and/or the current height and/or the current volume of the bleb, or on the basis of the injection time. Furthermore, the display can display a sought-after injection pressure as a target value for the injection pressure. In this way, a constant injection pressure can also be realized under manual control during the injection.

The method according to the invention for controlling the injection flow rate Q when injecting a fluid at an injection site between two tissue layers of the human eye with an increasing injection flow rate, for example between the neural layer of the retina and the retinal pigment epithelium, is distinguished in that injecting is carried out with an injection flow rate which increases during the injection for at least 30%, in particular at least 50%, preferably at least 65%, of the injection time or during the injection of at least 30%, in particular at least 50%, preferably at least 65% of the injection volume.

The method can be characterized by the following steps in particular: injecting is carried out with an initial injection flow rate below a defined upper limit value in a first step, and injecting is carried out with an injection flow rate increasing above the defined upper limit value in a second step. The method according to the invention has the advantages already mentioned. Within the scope of the first step, injecting can be carried out with a constant or a slightly increasing injection flow rate or with an injection flow rate varying as desired. It is crucial that the upper limit value is not exceeded in the first step.

The increase in the increasing injection flow rate may be limited by the maximum rate of change in the volume of a bleb that forms during the injection process. This can ensure that the increasing injection flow rate does not exceed the rate at which the volume of the bleb can change to accommodate the injected fluid. In this case, the maximum rate at which the volume of the bleb can change depends on the tissue separation rate.

The increasing injection flow rate may be based on a predetermined tissue separation rate that does not exceed a critical tissue separation rate. The critical tissue separation rate can be used to reliably predict the maximum possible change in the bleb volume on the basis of the radius of the bleb, the height of the bleb, or the time. By specifying a tissue separation rate that does not exceed the critical tissue separation rate, it is possible to ensure that the injection flow rate does not exceed the rate of change of the volume of the bleb in the case of its current volume. A parameter value representing the current volume of the bleb, for example the radius or the height, which corresponds on average to 0.54*r, may be recorded repeatedly and the respective value of the increasing injection flow rate can be determined on the basis of the parameter value recorded in each case.

The increasing injection flow rate can be subject to open-loop and/or closed-loop control in accordance with a predetermined curve of the injection flow rate as a function of at least one parameter. In this case, an injection flow rate resulting from a predetermined curve of the injection flow rate as a function of at least one parameter is preferably not exceeded. The open-loop and/or closed-loop control, in particular in the second step, can also be implemented according to a predetermined characteristic curve. The transition from the first to the second step can be manual or automated.

The described method according to the invention can be carried out by means of an already described apparatus according to the invention for injecting a fluid and/or by means of an already described arrangement for performing an ophthalmic operation. The method has the features and advantages already specified above. In particular, injecting can be carried out with an injection flow rate of no more than 5 microliters per second, for example no more than 1 microliter per second and preferably no more than 0.25 microliters per second, or less, in the first step. Furthermore, further injecting can be carried out with a quadratically increasing injection flow rate in the second step.

In the context of the method according to the invention, the current radius of the bleb can be recorded and the injection rate can be subject to such open-loop and/or closed-loop control in the second step that the fluid is injected at an increasing injection flow rate, which is increased proportionally to a power n of the radius r of the bleb, where the power n is greater than 1 and no more than 2. In this case, the proportionality factor is based on the predetermined tissue separation rate dr/dt. In other words, the increasing injection flow rate as a function of the radius of the bleb can be increased according to a polynomial increase. Preferably, the increasing injection flow rate as a function of the radius and/or the volume of the bleb can be controlled in such a way that the injection flow rate resulting from a curve for the injection flow rate as a function of the radius of the bleb and/or the volume of the bleb at the predetermined tissue separation rate is not exceeded for the respective radius and/or the respective volume. The increasing injection flow rate can also be controlled as a function of time, in such a way that an injection flow rate resulting from a defined curve is set and/or not exceeded for each point in time from the start of the injection.

The invention is explained in greater detail below on the basis of exemplary embodiments with reference to the accompanying figures. Although the invention is more specifically illustrated and described in detail by means of the preferred exemplary embodiments, nevertheless the invention is not restricted by the examples disclosed and other variations can be derived therefrom by a person skilled in the art, without departing from the scope of protection of the invention.

The figures are not necessarily accurate in every detail and to scale, and can be presented in enlarged or reduced form for the purpose of better clarity. For this reason, functional details disclosed here should not be understood to be limiting, but merely to be an illustrative basis that gives guidance to a person skilled in this technical field for using the present invention in various ways.

The expression "and/or" used here, when it is used in a series of two or more elements, means that any of the elements listed can be used alone, or any combination of two or more of the elements listed can be used. For example, if a structure is described as containing the components A, B and/or C, the structure can contain A alone; B alone; C alone; A and B in combination; A and C in combination; B and C in combination; or A, B, and C in combination.

FIG. 1 schematically shows a bleb arising during a subretinal injection.

Figure 2:
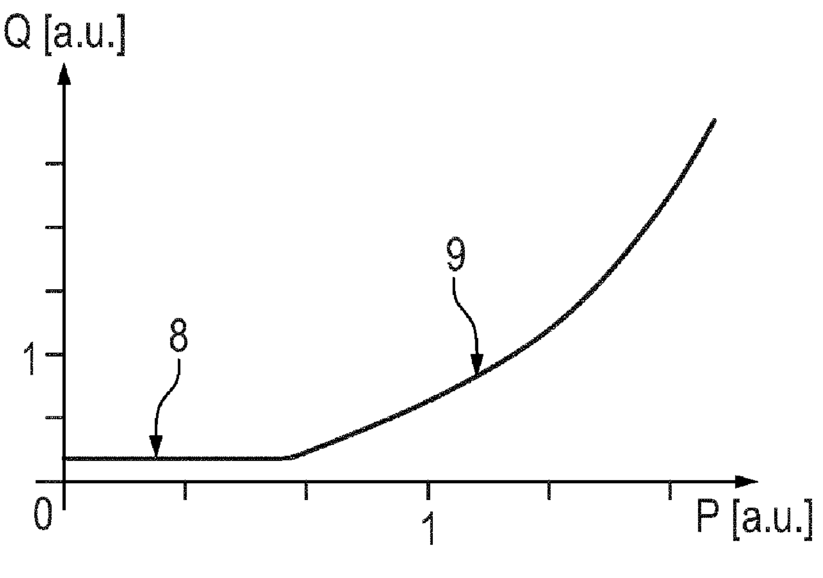

FIG. 2 schematically shows a first variant of open-loop or closed-loop control of the injection flow rate in the form of a diagram.

Figure 3:
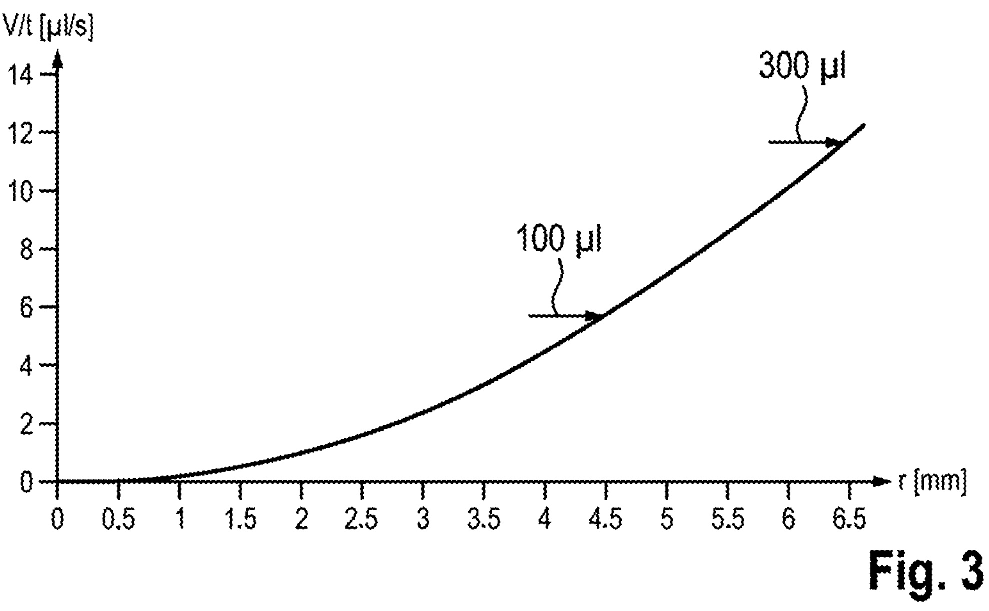

FIG. 3 schematically shows a curve for open-loop or closed-loop control of the injection flow rate on the basis of the bleb radius.

Figure 4:
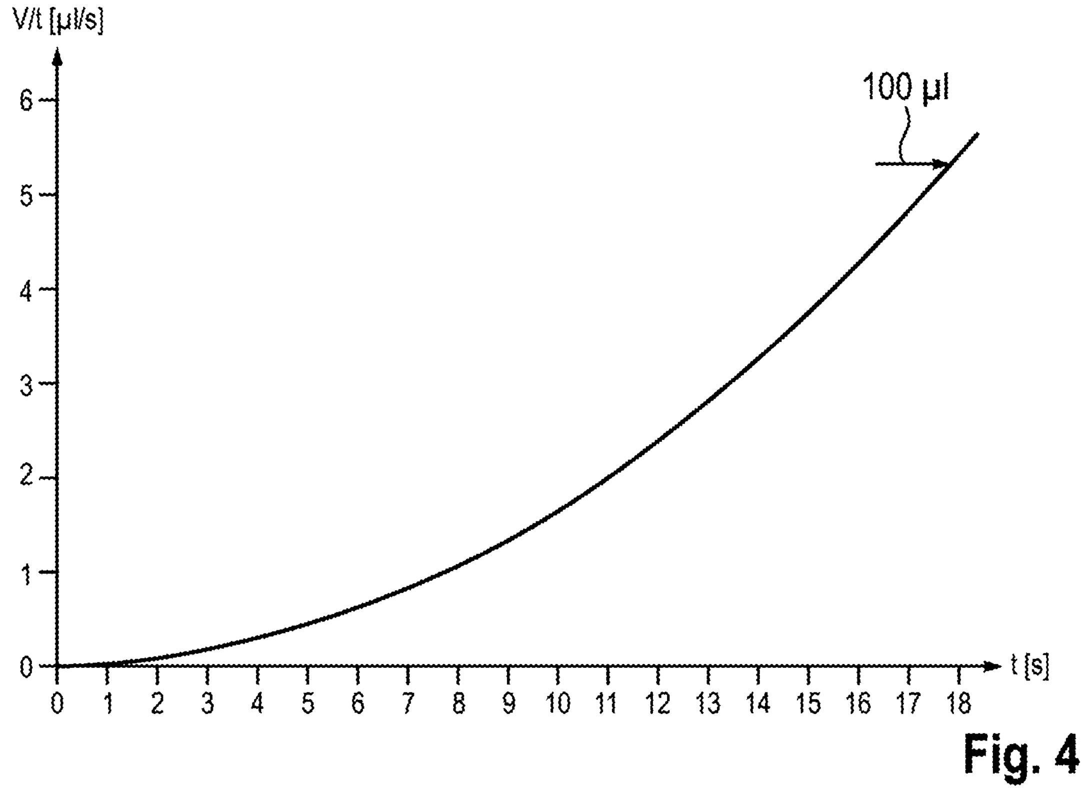

FIG. 4 schematically shows a curve for open-loop or closed-loop control of the injection flow rate on the basis of the time.

Figure 5:
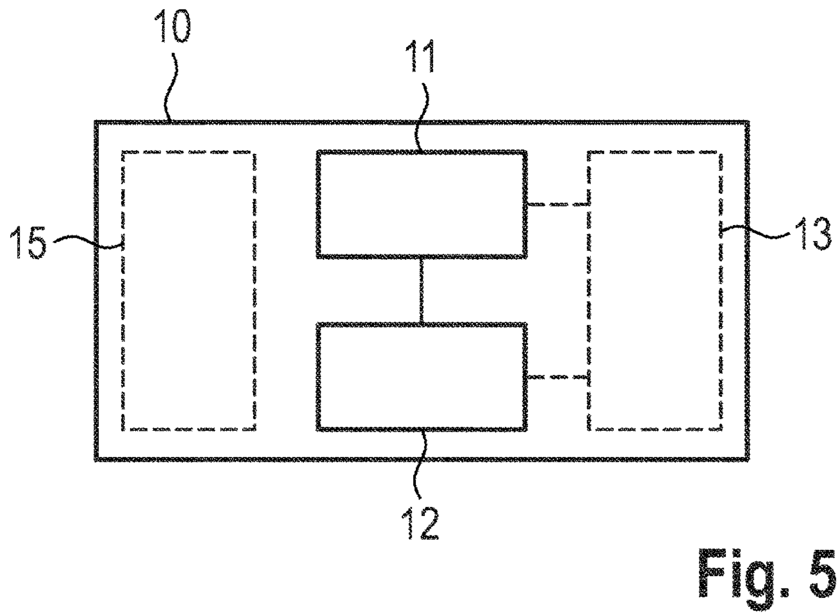

FIG. 5 schematically shows a control apparatus according to the invention.

Figure 6:
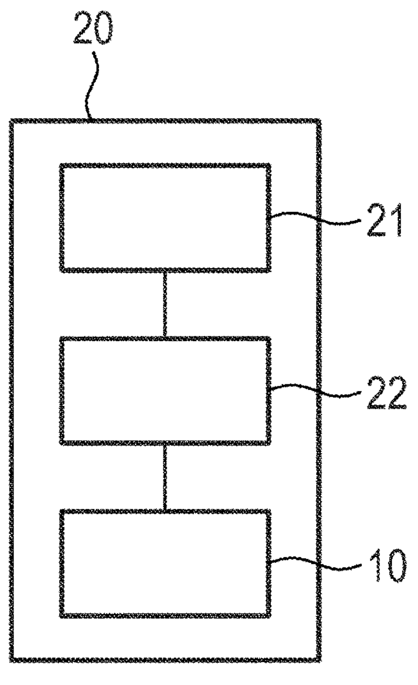

FIG. 6 schematically shows an apparatus according to the invention for injecting a fluid.

Figure 7:
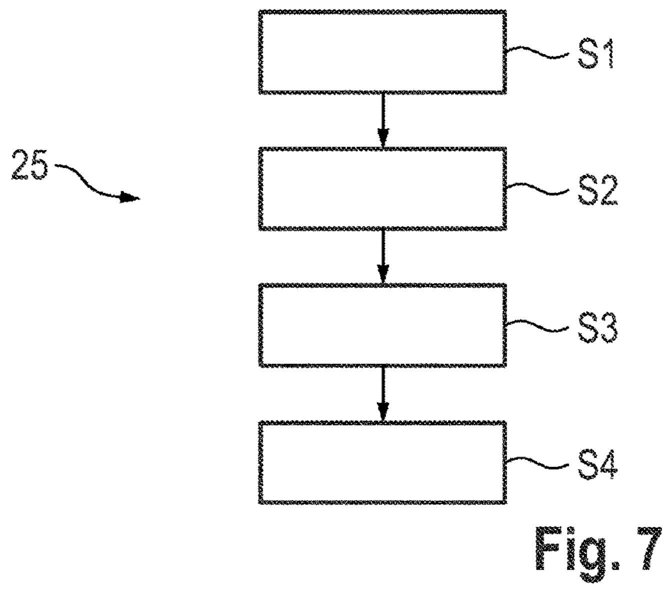

FIG. 7 schematically shows a first exemplary embodiment of a computer program according to the invention.

Figure 8:
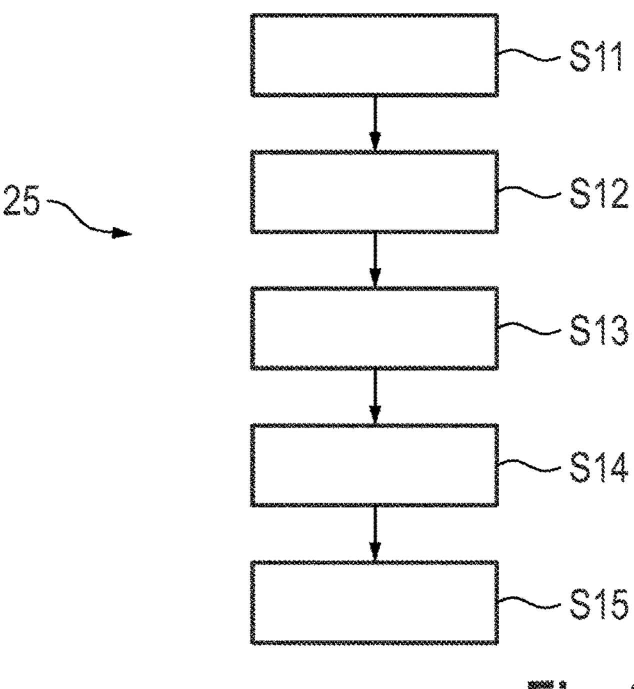

FIG. 8 schematically shows a second exemplary embodiment of a computer program according to the invention.

Figure 9:
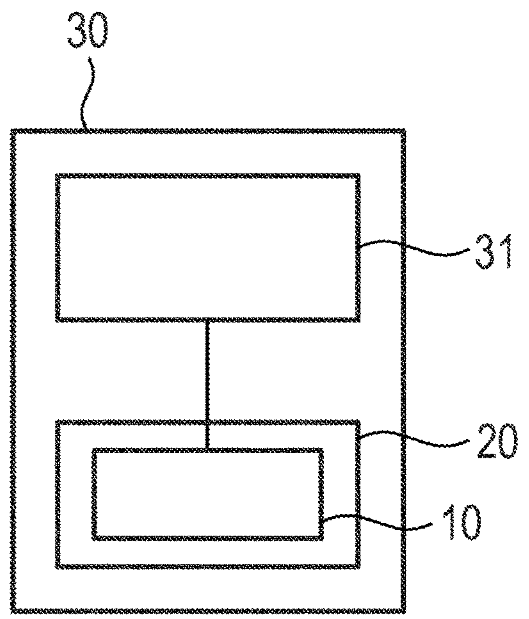

FIG. 9 schematically shows an arrangement according to the invention for performing ophthalmic operations.

Figure 10:
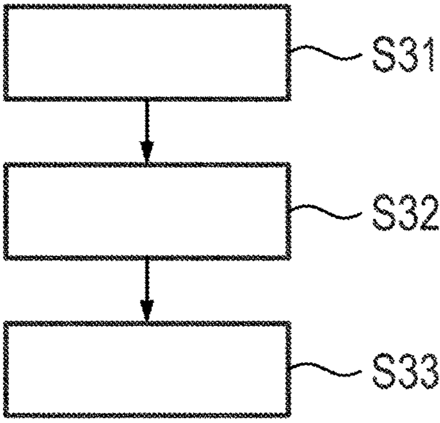

FIG. 10 schematically shows a method according to the invention for controlling the injection flow rate, in the form of a flowchart.

FIG. 1 schematically shows a bleb arising during a subretinal injection. In the case of a subretinal injection, liquid is injected at an injection site 5 between the neural layer of the retina 2 and the retinal pigment epithelium 3 by way of a cannula 4 which is part of a microsyringe (not depicted). Instead of a liquid, another fluid, such as a gas, for example, can also be injected. In the process, the neural layer of the retina 2 separates from the retinal pigment epithelium 3 with a tissue separation rate dr/dt. A liquid-filled bubble 1, a so-called bleb, forms during the injection. The bleb 1 has a volume V, a height c, and a radius r. The arrows 6 mark the direction of the radial increase during the injection. The leakage flow typically occurring during the injection but undesirable is identified by an arrow with the reference numeral 7. This leakage flow 7 in the region of the injection site 5 is reduced by means of the present invention. To this end, the injection flow rate during the injection, that is to say the injection rate on the basis of the bleb radius r, can be subject to open-loop and/or closed-loop control, preferably in such a way that injecting is initially carried out at a low, constant injection flow rate, for example until a perceptible bleb forms, and then the injection flow rate is increased. In this case, a predetermined tissue separation rate is preferably not exceeded.

For a better understanding of the invention, the relationship between the tissue separation rate and the injection flow rate is explained below. In a model presented below in exemplary fashion, the rate of the separation of the tissue layers corresponds to an increase in the lateral radius r of the bleb (see FIG. 1). From this, conclusions are drawn in the present case that the formation of the bleb takes the least amount of time if it is possible to maintain, but not exceed, a critical tissue separation rate, where possible over the entire injection process, in order to avoid volume loss of the injection liquid.

The inventive concept underlying the present invention is based on the fact that a low initial injection flow rate can be greatly increased as the bleb radius increases, with the tissue separation rate and thus the internal pressure of the bleb being able to be kept constant. This can be illustrated with the following model. The volume of the bleb can, for example, be described approximately as half an ellipsoid, for whose volume V the following applies:

$$V_{half\_ellipsoid} = \frac{\frac{4\pi}{3} * a * b * c}{2} = \frac{4}{6}\pi * a * b * c \quad \text{(Equation 1)}$$

The radii a and b of the ellipsoid in x- and y-direction have been assumed here to be equal (a=b=r, r-radius). The height of the bleb c can be given or determined on average by 0.54 times the radius r. The stated value for c=0.54*r was determined from OCT images. This results in the following for the change in the volume V over time t, that is to say the injection flow rate Q:

$$\frac{dV_{half\_ellipsoid}}{dt} = Q = 1.08\pi * r^2 * \frac{dr}{dt} \quad \text{(Equation 2)}$$

In this context, dr/dt corresponds to the tissue separation rate, that is to say the increase in the radius r over time t.

Equation 2 shows that the rate at which the volume of the bleb can change is proportional to the square of its radius, where the proportionality factor is given by the tissue separation rate dr/d, up to a constant factor. If the increasing injection flow rate is controlled in such a way that the change in volume resulting from equation 2—and hence the capacity of the bleb—is not exceeded, leakage of the injected liquid through the puncture site can be avoided or at least greatly reduced in comparison with the prior art.

In order to determine a control curve that represents an increasing injection flow rate as a function of the radius of the bleb, for which the capacity of the bleb is not exceeded, the critical tissue separation rate, which should not be exceeded during the injection in order to avoid a leakage flow, is still required. The critical tissue separation rate for separating the neuroretina from the retinal pigment epithelium can be determined by investigations, for example using OCT scans.

The critical tissue separation rate is the separation rate for which the lowest volume loss occurs. A critical separation rate of 0.26 millimeters per second (0.26 mm/s) was determined in experiments on pig eyes. From equation 2, the graph of the gradient of the increasing injection flow rate as a function of the bleb radius can be determined by virtue of inserting increasing values for the radius r and the critical tissue separation rate. An example of such a curve is shown in FIG. 3, which is further described below. The time dependence of the injection flow rate for an injection without volume loss is depicted in exemplary fashion in FIG. 4 and is further described in detail below.

FIG. 2 schematically shows a first variant of open-loop or closed-loop control of the injection flow rate in the form of a diagram. A parameter P is plotted on the x-axis in arbitrary units [a.u.] and the specified injection flow rate Q, that is to say the injection flow rate to be set, is plotted on the y-axis in arbitrary units [a.u.], for example microliters. By way of example, the parameter P can be the radius r or the diameter of the bleb or the time. In an optional first step or an optional first operating mode, liquid is injected at a constant or slightly increasing initial injection rate, which does not exceed a predetermined upper limit value during the entire first step or during the entire first operating mode. This upper limit value is 5 microliters per second in an exemplary embodiment variant. However, it may also be lower, in particular 1 microliter per second or 0.1 microliter per second or 0.05 microliter per second. This step or operating mode is identified by the reference numeral 8. Then, in a second step, which can also be the only step, or a second operating mode, which might likewise be the only operating mode, which is identified by the reference numeral 9, the injection flow rate is increased above the upper limit value in accordance with the predetermined injection flow rate. The increase can be linear with a gradient in the range from 2 to 100 or with a polynomial dependence, preferably a quadratic dependence as in equation 2, that is to say in accordance with a parabola.

The transition from the first step or operating mode to the second step or operating mode may be implemented manually, for example when a bleb is clearly visible, or in automated fashion, for example after a defined time or when the bleb reaches a defined radius, or in accordance with a characteristic curve.

A curve for open-loop or closed-loop control of the increasing injection flow rate on the basis of the bleb radius r, for example within the scope of the second step or operating mode, is shown schematically in exemplary fashion in FIG. 3 for a sought-after tissue separation rate of 0.26 mm/s according to equation 2. The x-axis plots the bleb radius r in millimeters (mm) and the y-axis plots the predetermined injection flow rate V/t in microliters per second (µl/s). According to the curve shown in FIG. 3, the specified injection flow rate in this case increases proportionally with the square of the radius r of the bleb. The tissue separation rate (dr/dt) is included in the proportionality factor associated with the square of the radius r, as can be seen from equation 2. The bleb radii at which 100 µl and 300 µl have been injected are indicated by arrows.

The time dependence of the predetermined increasing injection flow rate Q=V/t for a corresponding injection is shown schematically in FIG. 4. In FIG. 4, the time tin seconds s is plotted on the x-axis and the predetermined increasing injection flow rate V/t in microliters per second μl/s is plotted on the y-axis.

FIG. 5 schematically shows a control apparatus according to the invention for open-loop and/or closed-loop control of an injection flow rate when injecting a liquid at an injection site 5 between two tissue layers of the human eye, for example between the neural layer of the retina 2 and the retinal pigment epithelium 3. The apparatus 10 comprises an open-loop or closed-loop control unit designed for control of the injection flow rate, in such a way that the injection flow rate increases during the injection for at least 30% of the injection time or during the injection of at least 30% of the injection volume.

The open-loop or closed-loop control unit can in particular be designed for such control of the injection flow rate that an initial injection 11 occurs with a defined upper limit value for the initial injection flow rate, followed by an injection 12 with an injection flow rate increasing above the defined upper limit value. In an exemplary variant, the control apparatus 10 comprises a first operating mode 11, which is designed to provide a predetermined, for example constant, injection flow rate 8 below the defined upper limit value. In this variant, the apparatus 10 moreover comprises a second operating mode 12, which is designed to provide a curve with an injection flow rate 9 that increases depending on a parameter P, for example depending on the radius r of the bleb 1. Within the scope of the control, this curve describes the injection flow rate Q that is predetermined, that is to say to be set, on the basis of the parameter and is selected in such a way that a by equation 2 with a predetermined tissue separation rate dr/dt inserted therein is not exceeded. The predetermined tissue separation rate is less than or equal to the critical tissue separation rate in this case.

The control apparatus 10 may comprise a display 15. The currently used injection flow rate can be provided in the form of an output by means of the display 15. In particular, target values and actual values can be displayed, with the injection flow rate predetermined for the current value of the parameter P representing the target value and the currently used injection flow rate representing the actual value. The actual values can then be subjected to open-loop or closed-loop control in manual or automated fashion with respect to the target values.

In an advantageous variant, the control apparatus 10 can be designed to control the increasing injection flow rate Q=V/t in connection with a recorded current value of a parameter, which characterizes the current radius r of the bleb 1 in the present exemplary embodiment, in such a way that the liquid is injected at an injection flow rate that is increased proportionally to a power n of the radius r of the bleb ($Q \sim r^n$), where the power n>1 and is no more than 2 (1<nß2). In the present exemplary embodiment, n=2. Depending on whether the specified tissue separation rate that is included in the proportionality factor is less than or equal to the critical tissue separation rate, the increasing injection flow rate runs along or below a curve as shown in FIG. 3 in exemplary fashion. If the power n is chosen between 1 and less than 2, the resulting curve of the increasing injection flow rate as a function of the bleb radius would run below a curve shown in FIG. 3 in exemplary fashion, even if the predetermined tissue separation rate included in the proportionality factor is equal to the critical tissue separation rate. In any case, according to the curve, the injection flow rate can increase continuously with increasing bleb radius during the injection without a relevant leakage flow of the liquid to be injected occurring.

Instead of a parameter that characterizes the current radius r of the bleb, a parameter that characterizes the current height c of the bleb can also be recorded. The height c of the bleb is related to its radius r via c=0.54*r, and so the radius can be determined from the height.

In a further exemplary variant, the control apparatus 10 is designed, in addition or as an alternative to the above-described variants, for control of the injection flow rate as a function of time t, in such a way that an injection flow rate resulting from a defined curve is set and/or not exceeded for each point in time t from the start of the injection. The injection flow rate can be controlled, for example, along or below a curve shown in exemplary fashion in FIG. 2 or FIG. 4.

A closed-loop control apparatus can also be used instead of the open-loop control apparatus. It is then designed to determine and provide the increasing injection flow rate on the basis of the determined current tissue separation rate and a predetermined tissue separation rate. To determine the increasing injection flow rate, the control apparatus 10 then initially determines a deviation of the determined current tissue separation rate from the predetermined tissue separation rate and then determines the increasing injection flow rate Q on the basis of the previously determined deviation, in such a way that the current tissue separation rate reaches the predetermined tissue separation rate. If the predetermined tissue separation rate corresponds to the critical tissue separation rate, then the closed-loop control essentially causes the injection flow rate to follow the curve of FIG. 3; if the predetermined tissue separation rate is below the critical tissue separation rate, then the increasing injection flow rate is below the curve shown in FIG. 3.

To determine the current value of the at least one parameter, the control apparatus 10 designed as a closed-loop control apparatus comprises at least one device 13 for recording the current value of the at least one parameter that characterizes the current tissue separation rate, or such an apparatus is connected to the control device 10 for signal transmission purposes. In an exemplary embodiment, the device 13 for recording the current value of the at least one parameter is a surgical microscope, by means of which a chronological sequence of images is recorded. The rate of change dr/dt of the radius of the bleb, which represents the current tissue separation rate, can then be determined from the chronological sequence of images using image evaluation software. Instead of the rate of change dr/dt of the radius of the bleb, the device 13 for recording the current value of the at least one parameter may also record other parameters which are suitable for representing the current tissue separation rate, for instance the rate of change of the height c of the bleb, which on average corresponds to 0.54 times the radius r. Other parameters uniquely associated with the tissue separation rate are also conceivable.

As already mentioned, the device 13 can be, in particular, an apparatus for generating an image of the injection site, for example a microscope, for instance a surgical microscope. In this case, the apparatus for generating an image of the injection site 5 is preferably designed to provide information about properties of a bleb 1 arising during the injection, for example the volume and/or the height of the bleb and/or the radius of the bleb. This information can be provided, for example, using digital image evaluation routines that are applied to an image obtained with a microscope in order to identify the bleb and its radius r in the image. By contrast, using a coherence tomography device, the height c of the bleb can be determined from a scan along the z-axis of the coherence tomography device (z-scan).

As an alternative to a microscope, an optical coherence tomography device can be present, or functionally connected to the open-loop or closed-loop control apparatus, as the device 13 for recording the current value of the at least one parameter. Using an optical coherence tomography device, the height c of the bleb in particular can be determined by means of what is known as a z-scan.

In a further alternative, the at least one device 13 for recording the current value of the at least one parameter can be designed to record an injection parameter. The device 13 for recording the current value of the at least one parameter can be designed, for example, as a pressure sensor for determining the injection pressure, that is to say the pressure of the injected liquid. If the injection flow rate Q is too high, the tissue separation rate is not sufficient to increase the radius of the bleb—and hence its volume—quickly enough so that the entire quantity of liquid injected per unit time is easily accommodated in the bleb. As a result, the injection pressure required to inject the quantity of liquid into the bleb increases, leading to an increase in the pressure in the bleb and hence an increase in the leakage flow. Then again, if the injection flow rate is low enough, the tissue separation rate is sufficient to create the space in the bleb for all of the liquid injected per unit time. The injection pressure required to inject the quantity of liquid into the bleb does not have to be increased in that case.

This allows closed-loop control of the injection flow rate, in such a way that the injection pressure required for injecting a predetermined quantity of liquid per unit time is measured and its deviation from an injection pressure predetermined for this quantity of liquid per unit time is determined. The injection pressure is then returned to the predetermined injection pressure on the basis of the deviation, and so the entire injection is implemented with a constant injection pressure. In this case, the predetermined injection pressure is dimensioned such that the injection flow rate resulting therefrom is low enough for the tissue separation rate to enable such an increase in volume of the bleb that the entire quantity of liquid injected per unit time is easily accommodated in the bleb. Since the volume of the bleb over time changes with the square of its radius, the constant injection pressure causes the injection flow rate to increase over time in accordance with FIG. 4. This ensures that the injection flow rate follows the curve from FIG. 4 or is below it, depending on whether the predetermined injection pressure is an injection pressure that leads to a tissue separation rate corresponding to the critical tissue separation rate (injection flow rate Q follows the curve) or corresponding to a smaller tissue separation rate (injection flow rate Q is below the curve).

FIG. 6 schematically shows an apparatus for injecting a liquid at an injection site between two tissue layers of the human eye, for example between the neural layer of the retina and the retinal pigment epithelium. The apparatus 20 comprises a microsyringe 21, which has a cannula 4, for example, and an actuation device 22 for actuating the microsyringe 21. In the present exemplary embodiment, the actuation device 22 has a foot pedal. However, it may also have a manual control. The apparatus 20 furthermore comprises a control apparatus for open-loop or closed-loop control of the injection flow rate 10, for example in an embodiment variant shown in FIG. 5. The actuation device 22 may also comprise the control apparatus 10. Preferably, the actuation device 22 is designed to pneumatically provide a pressure of between 10 and 2000 mmHg or between 0.013 and 2.67 bar.

A flowchart of a first exemplary embodiment of the computer program according to the invention is shown schematically in FIG. 7. In the present exemplary embodiment, the computer program 25 contains instructions which, when executed on a computer, cause the latter to read in the current value of a parameter in a first step S1. This parameter can be, for example, the duration of the injection so far, the radius of the bleb, the height of the bleb, etc.

In step S2, there first of all is, on the basis of the current value of the parameter read in step S1, an injection with an initially low injection flow rate which does not exceed a predetermined upper limit value of 1 microliter per second in the present exemplary embodiment. However, the predetermined upper limit value may also be lower, for example 0.5 microliter per second, 0.1 microliter per second or 0.05 microliter per second. Step S2 continues until a predetermined value for the parameter, for example a predetermined injection duration, a predetermined radius of the bleb or a predetermined height of the bleb, is reached.

Once the predetermined value for the parameter has been reached, the injection is implemented in step S3 with an injection flow rate increasing above the predetermined upper limit value. In this case, injecting is implemented with an injection flow rate assigned to the respective value of the parameter. The injection flow rate assigned to the respective value of the parameter can be determined using a table stored in the memory of the computer, which table assigns a respective injection flow rate to values for the parameter. Alternatively, a calculation rule can be stored in the computer, which calculation rule allows an injection flow rate to be calculated on the basis of the current value of the parameter. The calculation rule can be given by equation 2, for example. Equation 2 can also be used to create the aforementioned table.

Finally, in step S4, there is the generation and output of an adjustment signal for the actuation device 22 of the apparatus for injecting a liquid or another fluid at an injection site between two tissue layers of the human eye, for example between the neural layer of the retina and the retinal pigment epithelium.

A flowchart of a second exemplary embodiment of the computer program according to the invention is shown schematically in FIG. 8. The computer program 25 according to the second exemplary embodiment contains instructions which, when executed on a computer, cause the latter in a first step S11 to carry out an injection with an initially low injection flow rate which, in the present exemplary embodiment, does not exceed a predetermined upper limit value of 1 microliter per second. However, the predetermined upper limit value may also be lower, for example 0.5 microliter per second or 0.25 microliter per second. In addition, the recorded current value of a parameter is started to be read in, which current value of a parameter indicates a current tissue separation rate of the separation of two tissue layers of the human eye, for example between the neural layer of the retina 2 and the retinal pigment epithelium 3, when injecting a liquid or another fluid at an injection site 5 between the tissue layers. By way of example, this parameter can be the change in the radius of the bleb over time, the change in the height of the bleb over time, or the change in the volume of the bleb over time, the injection pressure, etc.

On the basis of the current value of the parameter read in step S11, the current tissue separation rate is calculated in step S12, which is then compared to a predetermined tissue separation rate in step S13 in order to determine the deviation of the current tissue separation rate from the predetermined tissue separation rate. Then, after a predetermined period of time has elapsed, a control signal is generated in step S14 in the present exemplary embodiment on the basis of the determined deviation and it leads to a reduction in the deviation in order to adapt the current tissue separation rate to the predetermined tissue separation rate. In step S15, the control signal is then output to the actuation device 22 of the apparatus for injecting a liquid or another fluid at an injection site between two tissue layers of the human eye, for example between the neural layer of the retina and the retinal pigment epithelium. The closed-loop control then leads to an injection with an injection flow rate increasing above the predetermined limit value after the predetermined period of time taking place.

FIG. 9 schematically shows an arrangement according to the invention for performing ophthalmic operations. The arrangement 30 includes a device for generating an image of the injection site 5, which is identified by the reference numeral 31. This may be a microscope, for example a surgical microscope, and/or an optical coherence tomography device, for example an intraoperative optical coherence tomography device. The arrangement 30 further comprises an apparatus according to the invention for injecting a fluid, for example a liquid or a gas, at an injection site 20, which apparatus may be, for example, an apparatus 20 shown schematically in FIG. 6. The device 31 for generating an image of the injection site can also be the device for generating an image shown in FIG. 5. In the variant shown in FIG. 9, the device for generating an image of the injection site 31 is connected to the control apparatus 10 for signal transmission purposes.

FIG. 10 schematically shows, in the form of a flowchart, a variant of a method according to the invention for control of the injection flow rate Q when injecting a fluid at an injection site between two tissue layers of the human eye, for example between the neural layer of the retina 2 and the retinal pigment epithelium 3. In an optional step S31, a characteristic curve for controlling the injection flow rate or a reference variable for closed-loop control of the injection flow rate is predetermined. By way of example, the characteristic curve may represent the injection flow rate as a function of the current radius r of the bleb, the current volume V of the bleb, the current height c of the bleb, the duration of the injection, etc. By way of example, the reference variable can be a predetermined tissue separation rate dr/dt, wherein it may in particular be the critical tissue separation rate, or a predetermined injection pressure. The predetermined tissue separation rate or the predetermined injection pressure can be determined, for example determined experimentally, in advance.

In a first step S32 of the method, the fluid is injected at an injection flow rate below a defined upper limit value, for example at a constant injection flow rate. In a subsequent second step S33, injecting is carried out with an increasing injection flow rate, for example on the basis of the predetermined characteristic curve if the injection flow rate Q=dV/dt is subject to open-loop control or on the basis of the predetermined reference variable if the injection flow rate is subject to closed-loop control. In this case, the increasing injection flow rate can be determined as described above.

The described method can be carried out using the above-described apparatuses according to the invention and the arrangement according to the invention for performing ophthalmic operations. In particular, the open-loop or closed-loop control of the injection flow rate can be implemented along a curve analogous to those shown in exemplary fashion in FIGS. 2 to 4.

A specific embodiment variant of the present invention is described below. An ophthalmic microscope is used, preferably with intraoperative OCT (optical coherence tomography), in this application variant. Furthermore, an ophthalmological console for posterior segment interventions is available, which can pneumatically provide a pressure of 10 to 2000 mmHg. In addition, there is an actuation device which comprises a foot pedal for controlling the injection. Moreover, the arrangement comprises a micro-injection system, which comprises a microsyringe, for example with a total volume of 1 ml. The micro-injection system can be connected to a console. A 41G injection cannula, which is attached to the aforementioned injection syringe, can be used as the injection cannula.

An injection may comprise the following steps: Drawing up 100 μl of injection liquid into the syringe, piercing into the pars plana region of the eye with the cannula through a trocar, having previously removed the vitreous body by vitrectomy, piercing the cannula into the neuroretina, but without penetrating through the retinal pigment epithelium.

In a first embodiment variant, the injection flow rate can be controlled by the user by visual inspection. By way of example, the foot pedal can be brought by the user from a first position, in which no injection flow is provided, to a second position, whereby the liquid is injected at an injection flow rate of, for example, 0.25 μl per second or less. As soon as the user observes that a clearly recognizable bleb is formed, for example at a mean diameter of 0.5 mm, wherein it may be an average of a diameter measured in an x-direction and a y-direction, the foot pedal is brought into a third position. What needs to be considered here is that the tissue separation rate used for equation 2 is no more than 1 mm/s, but preferably less than 0.5 mm/s down to 0.01 mm/s or less, in order to account for the higher adhesive forces of retinal pigment epithelium and neuroretina. Once the desired volume has been injected, the foot pedal is returned to the first position.

In a second embodiment variant, after the foot pedal has been brought into the third position, a target value and an actual value for the injection flow rate can be displayed on the console, for example on a display, which may be part of a control apparatus 10 used according to the invention. In this case, the target value can be determined and made available, as described above, for example calculated using equation 2. The user can now control the injection flow rate by means of a further signal using the foot pedal, for example by way of a rotational movement or by tilting the pedal to a greater or lesser extent in a third pedal position. On the basis of the current injection flow rate displayed, the user can recognize here how the actual value, set by them, deviates from the target value.

In a third embodiment variant, the injection flow rate can be subject to open-loop or closed-loop control by measuring geometric properties of the bleb. The closed-loop control can be implemented by way of a control loop which uses geometric properties of the bleb, for example the volume and/or the radius and/or the height, as input signal. To this end, a data connection is established between the microscope or the OCT and the console, in particular the vitrectomy console. As soon as the pedal has been brought into the second position and the injection has been started, the shape of the bleb, for example at least one of the aforementioned geometric properties, is measured and the volume is preferably determined. The injection flow rate can now be subject to open-loop or closed-loop control according to a curve shown in FIG. 2 or FIG. 3 or a corresponding curve.

In a fourth embodiment variant, the injection flow rate can be subject to closed-loop control on the basis of a pressure measurement, for example a measurement of the pressure within the bleb and/or the injection pressure. A pressure sensor can be attached as close as possible to the utilized cannula in the process. The fluidics are, for example, subject to such open-loop or closed-loop control that an injection pressure, which correlates with the defined tissue separation rate, in particular an upper limit value of the tissue separation rate, is kept constant. In this case, the injection flow rate is effectively subject to open-loop or closed-loop control according to one of the curves shown in FIG. 2 to 4 or analogous curves.

LIST OF REFERENCE SIGNS

1 Bleb
2 Neural layer of the retina
3 Retinal pigment epithelium
4 Cannula
5 Injection site
6 Increase in the radius
7 Leakage flow
8 Constant injection flow rate
9 Increasing injection flow rate
10 Control apparatus
11 Initial injection, first operating mode
12 Injection with increasing injection flow rate, second operating mode
13 Device for recording the current value of the at least one parameter which characterizes the current tissue separation rate
15 Display
20 Apparatus for injecting a liquid at an injection site between the neural layer of the retina and the retinal pigment epithelium
21 Microsyringe
22 Actuation device
25 Computer program
30 Arrangement for performing ophthalmic operations
31 Device for generating an image of the injection site
S1 Reading in the current value of a parameter
S2 Injecting with an initially low injection flow rate
S3 Injecting with an increasing injection flow rate
S4 Generating and outputting an adjustment signal for the actuation device
S11 Reading in the current value of a parameter
S12 Calculating the current tissue separation rate
S13 Comparing the current tissue separation rate with the predetermined tissue separation rate
S14 Generating a control signal
S15 Outputting a signal to the actuation device
S31 Specifying a characteristic curve
S32 Injecting with an injection flow rate below a specified upper limit value
S33 Injecting with an increasing injection flow rate
c Height
r Radius
V Volume
t Time
P Parameter
Q Injection flow rate

The invention claimed is:

1. A control apparatus for open-loop and/or closed-loop control of an injection flow rate when injecting a fluid at an injection site between two tissue layers of the human eye with an injection flow rate increasing over time, comprising:

an open-loop or closed-loop control unit designed for open-loop or closed-loop control of the injection flow rate, in such a way that the injection flow rate increases during the injection for at least 30% of the injection time or during the injection of at least 30% of the injection volume.

2. The control apparatus as claimed in claim 1, wherein:

an initial injection flow rate does not exceed a value of 5 microliters per second (μl/s) and/or a maximum injection flow rate achieved during the injection does not exceed a value of 100 μl/s and/or the open-loop or closed-loop control unit is designed for open-loop or closed-loop control of the increasing injection flow rate, in such a way that an injection takes place with a constant or variable gradient of between 2 and 100 and/or the increasing injection flow rate is controlled according to a predetermined curve of the injection flow rate as a function of at least one parameter.

3. The control apparatus as claimed in claim 1, wherein:

the control apparatus is designed to determine a current injection flow rate on the basis of the current value of at least one parameter that characterizes the current tissue separation rate of two tissue layers of the human eye and to provide said current injection flow rate as an increasing injection flow rate.

4. The control apparatus as claimed in claim 3, wherein:

the control apparatus is designed to determine a current injection flow rate and to provide the latter as an increasing injection flow rate at which a predetermined tissue separation rate is not exceeded.

5. The control apparatus as claimed in claim 3, further comprising:

a device for recording and/or displaying the current value of the at least one parameter which characterizes the current tissue separation rate, and/or the device for recording the current value of the at least one parameter is designed to record, as a parameter, a property of a bleb forming during the injection and/or an injection parameter.

6. The control apparatus as claimed in claim 5, wherein:

the device for recording the current value of the at least one parameter comprises an apparatus for generating an image of the injection site and/or a pressure sensor for determining the injection pressure.

7. The control apparatus as claimed in claim 1, wherein the control apparatus is designed for open-loop or closed-loop control of the increasing injection flow rate, in such a way that the predetermined tissue separation rate is not exceeded and/or that the tissue separation rate is kept constant and/or that the injection pressure is kept constant.

8. The control apparatus as claimed in claim 1, wherein:

the control apparatus is designed for open-loop and/or closed-loop control of the increasing injection flow rate, in such a way that the fluid is injected at an injection flow rate which is increased proportionally to a power n of the radius of the bleb, where the power n is greater than 1 and no more than 2, and the proportionality factor is based on the predetermined tissue separation rate, where Q denotes the injection flow rate, V denotes the volume of the bleb, and t denotes the time.

9. The control apparatus as claimed in claim 1, wherein: the control apparatus is designed, in conjunction with a current value of a parameter which characterizes the current radius r of a bleb forming during the injection and/or the current volume of the bleb, for open-loop and/or closed-loop control of the increasing injection flow rate on the basis of the radius and/or the volume of the bleb such that a the injection flow rate for the respective radius or the respective volume, which injection flow rate results from a curve for the injection flow rate on the basis of the radius and/or the volume of the bleb at the predetermined tissue separation rate, is not exceeded.

10. The control apparatus as claimed in claim 1, wherein: the control apparatus is designed for open-loop and/or closed-loop control of the increasing injection flow rate as a function of time, in such a way that an injection flow rate resulting from a defined curve is set and/or not exceeded for each point in time from the start of the injection.

11. A non-transitory computer-readable medium containing computer-readable instructions for open-loop and/or closed-loop control of an injection flow rate when injecting a fluid at an injection site between two tissue layers of the human eye with an increasing injection flow rate, wherein execution of the computer-readable instructions by one or more processors of a computer causes the one or more processors to carry out the step of: controlling the injection flow rate such that the injection flow rate increases during an injection for at least 30% of the injection time or during the injection of at least 30% of the injection volume.

12. A system for performing ophthalmic operations, which comprises a device for generating an image of the injection site and an apparatus for injecting a fluid at the injection site between two tissue layers of the human eye in such a way that the first layer separates from the second layer at a tissue separation rate and forms a bleb, the system comprising:

a microsyringe, an actuation device for actuating the microsyringe, and a control apparatus for open-loop and/or closed-loop control of the injection flow rate as claimed in claim 1, which is connected to or comprised by the actuation device, wherein the device for generating an image of the injection site is connected to the control apparatus or is comprised by the control apparatus for signal transmission purposes.

13. A method for open-loop and/or closed-loop control of an injection flow rate when injecting a fluid at an injection site between two tissue layers of the human eye with an injection flow rate increasing over time, the method comprising:

injecting at an injection flow rate that increases during the injection for at least 30% of the injection time or during the injection of at least 30% of the injection volume.

14. The method as claimed in claim 13, wherein:

the injecting is carried out with an initial injection flow rate below a defined upper limit value in a first step, and the injecting is carried out with an injection flow rate increasing above the defined upper limit value in a second step.

15. The method as claimed in claim 13, wherein:

the increase in the increasing injection flow rate is restricted by the maximum rate of change in the volume of a bleb forming during the injection and/or the increasing injection flow rate is based on a predetermined tissue separation rate which does not exceed a critical tissue separation rate, and/or a parameter value representing the current volume of the bleb is recorded repeatedly and the respective value of the increasing injection flow rate is determined on the basis of the parameter value recorded in each case.

* * * * *